United States Patent

Arnoldy et al.

[11] Patent Number: 5,994,591
[45] Date of Patent: Nov. 30, 1999

[54] HYDROFORMYLATION PROCESS

[75] Inventors: Peter Arnoldy, Amsterdam, Netherlands; Cornelis Mark Bolinger, Sugar Land, Tex.; Eit Drent; Jan J. Keijsper, both of Amsterdam, Netherlands

[73] Assignee: Shell Oil Company, Houston, Tex.

[21] Appl. No.: 09/121,429

[22] Filed: Jul. 23, 1998

Related U.S. Application Data

[60] Provisional application No. 60/059,208, Sep. 18, 1997.

[51] Int. Cl.⁶ .................................................. C07C 45/50
[52] U.S. Cl. ........................................ 568/454; 568/451
[58] Field of Search .................................. 568/457, 454, 568/426, 429, 455

[56] References Cited

U.S. PATENT DOCUMENTS

| | | | |
|---|---|---|---|
| 3,876,672 | 4/1975 | Mrowca | 260/410.9 R |
| 4,390,729 | 6/1983 | Oswald | 568/454 |
| 4,792,636 | 12/1988 | Hensman et al. | 568/492 |
| 5,103,043 | 4/1992 | Drent et al. | 560/207 |
| 5,210,280 | 5/1993 | Drent | 560/204 |
| 5,214,220 | 5/1993 | Drent | 568/881 |
| 5,488,174 | 1/1996 | Drent et al. | 568/454 |

FOREIGN PATENT DOCUMENTS 9505354  2/1995  WIPO .

*Primary Examiner*—Gary Geist
*Assistant Examiner*—Sreeni Padmanabhan

[57] ABSTRACT

A process for the hydroformylation of ethylenically unsaturated compounds with carbon monoxide and hydrogen in the presence of a catalyst system comprising:

a) a source of palladium, platinum, or nickel cations;
b) a source of anions, other than halide anions, such as unsubstituted alkyl sulfonic acids, aryl sulfonic acids, perfluorinated alkyl sulfonic acids, perfluorinated aryl sulfonic acids, boric acid derivatives or alkylated versions thereof;
c) a source of at least one bidentate ligands of the formula $$R^1R^2M^1RM^2R^3R^4 \qquad (I)$$

wherein $M^1$ and $M^2$ independently represent a phosphorus, arsenic or antimony atom, R represents a bivalent bridging group containing from 1–4 atoms in the bridge, $R^1$ and $R^2$ together represent a bivalent cyclic group whereby the two free valencies are linked to $M^1$, and $R^3$ and $R^4$ independently represent a hydrocarbyl group, or together represent a bivalent cyclic group whereby the two free valencies are linked to $M^2$;

wherein said source of cations, anions, and ligands are selected to form a catalyst system having a solubility of at least $2 \times 10^{-4}$ mole of the cation a) per liter of a liquid mixture comprising said ethylenically unsaturated compound and the hydroformylation products;

and separating the hydroformylation products from the catalyst system in a solventless evaporative separator such as a falling film evaporator or a wiping film evaporator.

23 Claims, No Drawings

HYDROFORMYLATION PROCESS

This application claims the benefit of U.S. Provisional Application Ser. No. 60/059,208, filed Sep. 18, 1997, the entire disclosure of which is hereby incorporated by reference.

1. BACKGROUND OF THE INVENTION

This invention relates to a process for the hydroformylation of unsaturated hydrocarbons, and more specifically, to a process for hydroformylation in the presence of a catalyst system which is soluble to an amount of at least $2\times10^{-4}$ mole of the catalyst cation per liter of a liquid mixture of an ethylenically unsaturated compound feed and the hydroformylation product, followed by separating the hydroformylation reaction products from the catalyst system in a solventless evaporative separator.

2. FIELD OF THE INVENTION

In hydroformylation processes, carbon monoxide and hydrogen are reacted with an olefinic feed to produce the corresponding hydroxymethyl-substituted or formyl-substituted derivative of the olefin. These processes are of great industrial importance in converting olefins to aldehydes and alcohols. Other products such as esters, acids, and amides can generally be prepared in analogous processes by adding the carbonyl moiety or the hydroxymethyl moiety to one of the carbon atoms situated at a double bond of the olefin.

EP-B 0 495 547 and U.S. Pat. No. 5,488,174 describe a hydroformylation process which employs a catalyst system based on a source of palladium and a bidentate ligand of the formula $R_1R_2M_1RM_2R_3R_4$, in which $M_1$ and $M_2$ independently may be phosphorous, arsenic, or antimony atoms. R is a bivalent organic bridging group and $R_1$, $R_2$, $R_3$, and $R_4$, are unsubstituted or substituted aliphatic groups. One or more combinations of $R_1$, $R_2$, $R_3$, and $R_4$ can form a bivalent cyclic group. These ligands can include, for example, a 1,2bis(cyclooctylenephosphino) ethane (BCPE). According to U.S. Pat. No. 5,488,174, a halide acts as a catalyst promoter in this process. According to U.S. patent application Ser. No. 08/918,981 water acts as a co-promoter to the halide promoter.

The catalyst systems used in these processes typically employ strong acids as anion sources. Acids having a pKa of less than 3 (measured in aqueous solution at 18° C.) whose anions are non-coordinating or weakly coordinating with the metals of the platinum group have been found suitable for this purpose. Trifluoromethanesulphonic acid (TFMSA) has been the most preferred acid in this regard.

In the process described above, the catalyst and promoter are added to a reactor charged with olefin, hydrogen, and carbon monoxide. The products, unreacted reactants, and catalyst are later separated by a solvent extraction technique typically utilizing a sulfolane/olefin/alcohol medium. The sulfolane cosolvent allows the catalyst to be separated and recycled via phase separation. Thus, the solfolane is used as a phase-separating solvent.

Alternative separation methods might involve the use of solventless evaporative processes such as long tube vertical evaporators. The term "solventless" here refers to a distinction in the primary means by which separation occurs. A solventless evaporative process in this regard refers to a separation means in which one or more components of a liquor are separated primarily by virtue of their different boiling points. This is distinguishable from the reaction scheme identified above in which a sulfolane cosolvent facilitates the separation of liquor components by phase separation (i.e., as a function of solubility differences). Thus, a solvent-less evaporative separator process operates in the absence of a phase-separating solvent. The term does not mean that the reaction preceding the separation operates in the absence of any solvent. A hydroformylation process according to this invention could use any number of solvents to achieve purposes other than the primary facilitation of a separation of the products and/or intermediates involved in the process. For example, it could use olefins, alcohols and mixtures is thereof.

Falling film evaporator (FFE) or wiped film evaporator (WFE) are examples of solventless evaporative separation means which find utility in industrial processes. Such separation methods take in liquids (such as the liquor leaving a reactor) at the top of a vertical evaporator arrangement. The liquid flows down the wall of the evaporator as a film and is heated. Lower boiling materials will separate out as vapor with the higher boiling liquid component collecting (and/or withdrawn) at the bottom. Many industrial processes are already equipped with this type of separation process. It can be advantageous to use a FFE or WFE when the material to be distilled is thermally sensitive because the contact time for the working fluid is significantly shorter in these devices.

U.S. Pat. No. 5,488,174 does not disclose a hydroformylation process readily workable with a solventless evaporative separation process such as may be conducted in a FFE. That is, such a process has not been found to be capable of separating the catalyst from the hydroformylation products and unreacted reactants leaving the reactor. The catalyst has tended to decompose at the high temperatures at which it is necessary to conduct the separation. Furthermore, it is often undesirable to employ a cosolvent such as sulfolane. Sulfolane has a boiling point which is often inconveniently close to or overlapping with the boiling range of many desirable product alcohols. At the very least, this requires an additional means to separate and recycle the sulfolane to the process.

There has now been found a process for effectively removing a hydroformylation catalyst composition in a solventless evaporative product separation system without degrading the effectiveness of the catalyst.

3. SUMMARY OF THE INVENTION

The present invention is directed to a process for the hydroformylation of ethylenically unsaturated compounds with carbon monoxide and hydrogen in the presence of a catalyst system comprising:
a) a source of palladium, platinum, or nickel cations;
b) a source of anions, other than halide anions;
c) a source of at least one bidentate ligands of the formula $$R^1R^2M^1RM^2R^3R^4 \qquad (I)$$

wherein $M^1$ and $M^2$ independently represent a phosphorus, arsenic or antimony atom, R represents a bivalent bridging group containing from 1–4 atoms in the bridge, $R^1$ and $R^2$ together represent a bivalent cyclic group whereby the two•free valencies are linked to $M^1$, and $R^3$ and $R^4$ independently represent a hydrocarbyl group, or together represent a bivalent cyclic group whereby the two free valencies are linked to $M^2$;

wherein said source of cations, anions, and ligands are selected to form a catalyst system having a solubility of at least $2\times10^{-4}$ mole of the cation a) per liter of a liquid mixture comprising said ethylenically unsaturated compound and the hydroformylation products;

and separating the hydroformylation products from the catalyst system in a solventless evaporative separator.

Preferably, the solventless evaporator is a falling film evaporator or a wiped film evaporator.

In another embodiment of the invention, there is provided a hydroformylation process as above wherein the source of anions is derived from methane sulfonic acid, perfluorooctane sulfonic acid (PFOSA), and pentafluorobenzene sulfonic acid (PFBSA).

In yet another embodiment of the process, to the catalyst system is added a catalyst promoter such as a chloride, an iodide, a bromide, and in a further embodiment, water is also added as a catalyst co-promoter.

In a further embodiment of the process, there is provided a process for the hydroformylation of ethylenically unsaturated compounds with carbon monoxide and hydrogen in the presence of a catalyst system comprising:
a) a source of palladium, platinum, or nickel cations;
b) a source of anions, other than halide anions, comprising unsubstituted alkyl sulfonic acids, aryl sulfonic acids, perfluorinated alkyl sulfonic acids, perfluorinated aryl sulfonic acids, boric acid derivatives or alkylated versions thereof;
c) a source of at least one bidentate ligands of the formula

wherein $M^1$ and $M^2$ independently represent a phosphorus, arsenic or antimony atom, R represents a bivalent bridging is group containing from 1–4 atoms in the bridge, $R^1$ and $R^2$ together represent a bivalent cyclic group whereby the two free valencies are linked to $M^1$, and $R^3$ and $R^4$ independently represent a hydrocarbyl group, or together represent a bivalent cyclic group whereby the two free valencies are linked to $M^2$;
and separating the hydroformylation products from the catalyst system in a solventless evaporative separator.

4. DETAILED DESCRIPTION OF THE INVENTION

In broad terms, the process of this invention is conducted by contacting an ethylenically unsaturated feed with carbon monoxide and hydrogen in the presence of the catalyst system to form hydroformylation products, and then separating the hydroformylation products from the catalyst in a solventless evaporative separator.

Examples of suitable cation sources a) for use in the catalyst system are platinum or palladium compounds such as salts of palladium and nitric acid, sulphuric acid or sulphonic acids, salts of platinum or palladium and carboxylic acids with up to 12 carbon atoms, palladium- or platinum complexes, e.g. with carbon monoxide or acetylacetonate, or palladium combined with a solid material such as an ion exchanger or carbon. Palladium(II) acetate and platinum(II) acetylacetonate are examples of preferred metal sources.

The principle underlying the invention is that catalyst compositions of relatively low polarity are selected which will dissolve in the reaction system involved (feed used and product produced) to such a degree that they will remain in solution even in a solventless evaporative workout system. This principle can be satisfied in any or both of two ways, i.e. by selecting a suitable source of anions b) which is less polar than TFMSA and/or a suitable ligand c) which is less polar than BCPE. Notably, the combination of TFMSA (anion) and BCPE (ligand) in one catalyst composition is not effective when a solventless evaporative workout system is used.

As the source of anions b), any kind of compound less polar than TFMSA which generates anions may be used. Suitably, acids, or salts thereof, are used as source of anions, for example any of the acids mentioned above, which may also participate in the salts of the metals of the platinum group. Generally, anions of relatively low polarity are effective. Preferably, the source of anions b) has a pKa value of less than 3.

In another preferred embodiment, the anion source used in the catalyst composition according to the invention should have a boiling point, when measured at atmospheric pressure, of at least 50° C. above the boiling point of the hydroformylation product. More preferably, the boiling point 10 of the anion source is between 200 and 400° C.

Specific sources of anions b) which are less polar than TFMSA include unsubstituted alkyl sulfonic acids such as methane sulfonic acid, ethane sulfonic acid, propane sulfonic acid and octane sulfonic acid; aryl sulfonic acids such as p-toluene sulfonic acid; perfluorinated alkyl sulfonic acids such as perfluoro octane sulfonic acid; perfluorinated aryl sulfonic acids such as pentafluoro benzene sulfonic acid; boric acid derivatives such as $HBF_4$. $HB(C_6F_5)4$ and alkylated versions thereof. These anion sources may also be used in conjunction with a Lewis acid such as $BF_3$, $AlCl_3$, $SnF_2$, $Sn(CF_3SO_3)_2$, $SnCl_2$ or $GeCl_2$ or a combination of a Lewis acid with an alcohol. This will result in the formation of a complex anion.

Preferred anion sources are methane sulfonic acid (MSA), perfluoro octane sulfonic acid (PFOSA) and pentafluoro benzene sulfonic acid (PFBSA).

With respect to the source of bidentate ligand c), in its skeletal form as broadly defined above, M1 and M2 are preferably the same and, more preferably, they are both phosphorus atoms, in which case the ligands are bisphosphines.

The bridging group R is typically, though not necessarily, comprised of carbon atoms. It is preferred that they are $C_2$ or $C_3$ alkyl. The alkyl group includes alkyl groups which are substituted or unsubstituted and branched or unbranched. Exemplary organic bridging groups are $CH_2$—$CH_2$ and $CH_2$—$CH_2$—$CH_2$.

The bivalent cyclic group, which includes cyclic groups which are substituted or unsubstituted and branched or unbranched, represented by $R_1$ together with $R_2$, in general comprises at least 5 ring atoms and preferably contains from 6 to 9 ring atoms. More preferably the cyclic group contains 8 ring atoms. As a rule, all ring atoms are carbon atoms, but bivalent cyclic groups containing one or two heteroatoms in the ring, such as oxygen or nitrogen atoms, are not precluded. Examples of suitable bivalent cyclic groups are 1,4-cyclohexylene, 1,4-cycloheptylene, 1.3-cycloheptylene, 1,2-cyclooctylene, 1,3-cyclooctylene, 1,4-cyclooctylene, 1,5-cyclooctylene, 2-methyl-1,5-cyclooctylene, 2,6-dimethyl-1,4-cyclooctylene and 2,6-dimethyl-1,5-cyclooctylene groups.

Preferred bivalent cyclic groups are selected from 1,4-cyclooctylene, 1,5-cyclooctylene, and methyl (di)substituted derivatives thereof.

Mixtures of ligands comprising different bivalent cyclic groups may be used as well, e.g. mixtures of ligands with 1,4-cyclooctylene and ligands with 1,5-cyclooctylene groups.

$R_3$ and $R_4$ may independently represent various non-cyclic or cyclic groups, which includes cyclic groups which are substituted or unsubstituted, and branched or unbranched. Examples are alkyl groups such as ethyl, isopropyl, sec-butyl and tert-butyl groups, cycloalkyl groups such as cyclopentyl and cyclohexyl groups, aryl groups such as phenyl and tolyl groups and bivalent groups such as a hexamethylene group. Preferably, $R_3$, together with $R_4$ represents a bivalent cyclic group, in particular the same group as the group represented by $R_1$ together with $R_2$, in which case the two free valencies of the bivalent cyclic group are, of course, linked to $M_2$, instead of $M_1$.

Preferred examples of bidentate ligands to use when the source of anions b) is less polar than TFMSA include 1,2bis(1,4-cyclooctylene-phosphino)ethane, 1,2-bis(1,5cyclooctylenephosphino)ethane, their propane analogues, and mixtures thereof.

In the event that a polar source of anions b) is used such as TFMSA, then a source of ligands c) which is less polar than BCPE must be selected to impart a solubility to the catalyst of at least $2\times10^{-4}$ mole of the cation a) per liter of a liquid mixture comprising the ethylenically unsaturated feed compounds and the hydroformylation products. Alternatively, one may use a source of ligands c) which is less polar than BCPE in combination with a source of anions b) which is less polar than TRMSA.

Lowering the polarity of the source of ligands c) can be achieved by selecting ligands branched with non-polar groups on the skeletal backbone described above. For example, these branches can be placed on the skeletal bridging group R and/or on the bivalent cyclic group represented by $R_1$ and $R_2$ together, and/or on any of $R_3$ and $R_4$ when these are present separately, and/or on the bivalent cyclic group represented by $R_3$ and $R_4$ together, when present. The branches, individually, may be alkyl, cycloalkyl, aryl, alkylaryl or arylalkyl groups. They will preferably have from 1 to 30 chain linked atoms (not counting the hydrogen atoms), one or more of which may be hetero-atoms such as oxygen or nitrogen.

Bidentate ligands of this invention can be prepared in accordance with known techniques such as those disclosed in GB-A-1,127,965, incorporated herein by reference.

To measure whether or not the catalyst system selected will have a solubility of at least $2\times10^{-4}$ mole of the cation a) per liter of a liquid mixture comprising said ethylenically unsaturated compound and the hydroformylation product and whether such catalyst system is within the scope of the invention, the source of cations, anions, and ligands chosen are combined at a molar ratio of 1:2:1 and slurried at ambient temperature and atmospheric pressure with a 2:1 volume ratio of liquid mixture of the unsaturated compound feed and hydroformylated product. A filtered sample is then measured by HPLC to determine the extent of solubility.

The quantity of catalyst system used in the process of this invention may vary within wide limits. Usually, amounts in the range of $10^{-8}$ to $10^{-1}$, preferably in the range of $10^{-7}$ to $10^{-2}$ mole atom of platinum group metal per mole of ethylenically unsaturated compound are used. The amounts of the participants in the catalyst system are conveniently selected such that per mole atom of platinum group metal, from 0.5 to 10, preferably from 1 to 6 moles of bidentate ligand are used, and from 0.5 to 20, preferably from 1 to 8 moles of anion source or a complex anion source are used. It is more preferred that the process of this invention employs an anion to metal molar ratio of at least 2:1, more preferably greater than 2.3:1.

It is preferred that the process of this invention is practiced in the presence of a catalyst promoter. Halide anions are useful as promoters. Inorganic compounds including hydrogen halides such as HCl, HBr and HI may be used in this regard as well as metal halides such as NaCl, NaI, $MgBr_2$, $ZnCl_2$, $ZnI_2$, KBr, RbCl, CsCl, CsI, $MgI_2$ and CuCl. NaCl is the most preferred promoter.

Another category of recommended sources of halide anions consists of halogen containing organic compounds which are capable of providing halide anions to the reaction medium. For example, organic phosphonium halides, such as triarylalkyl phosphonium chloride and halogen containing aromatic compounds such as 5-halobenzoic acids, e.g. 5chlorobenzoic acid, 2,5-dichlorobenzoic acid, 2,3,5-triiodobenzoic acid, 3,5-di-iodobenzoic acid, m-halophthalic acids and esters thereof are all suitable.

The molar ratio between halide anions and platinum group metal cations is preferably not more than 3:1. If larger amounts of halide anions are present, the activity of the catalyst system tends to be adversely affected, presumably because of coordination occurring between palladium and halide moieties. Preferably, the molar ratio between halide anions and platinum group metal cations is at most 2:1, more preferably less than 1:1, for instance from 0.02:1 to 1:1. The additional presence of water, in an amount t of more than 0.6 wt % based on the total of the reaction mixture and up to its solubility limits under the reaction conditions, enhances the promoting effect of the halide promoter.

The ethylenically unsaturated compound, used as starting material, is preferably an olefin having from 2 to 30 carbon atoms per molecule, or a mixture thereof. They may comprise one or more double bonds per molecule. Preferred are internal olefins having from 4 to 24 carbon atoms, or mixtures thereof. Such olefin mixtures are commercially available, for example as products of a process for the oligomerization of ethylene, followed by a double bond isomerization and disproportionation reaction. In the process of the invention, these internal olefins, usually mixtures of linear internal olefins with 6 to 20 carbon atoms per molecule, or closer boiling fractions of such mixtures, can be hydroformylated at high rates and an almost complete conversion. Examples are mixtures of linear internal $C_6$ to $C_8$ olefins, and of linear internal $C_{10}$ to $C_{14}$ olefins. Substituted olefins may also be used, for example unsaturated carboxylic acids, esters of such acids, or unsaturated esters of carboxylic acids, e.g. allylacetate. If desired, branched olefins such as propene trimer or isomeric butene dimers (such as products of the well known "DIMERSOL" process) may be used, but the hydroformylation product will then, of course, contain branched structures as well. Olefinically unsaturated polymeric feedstock may also be used. This may include such materials as atactic polyolefins like 'Shube's' (mixture of oligomers of $C_{16}$-olefins), low molecular weight polyisobutylene (e.g., products commercially available from British Petroleum under the tradenames "NAPVIS" and "HYVIS"). Styrene-butadiene (block)copolymers may also be converted into interesting alcohols (as intermediates to synthetic lubricants, functionalized additives, etc.). Alphaolefins, such as 1 octene and propene, and diolefins, such as norbornadiene, dicyclopentadiene, 1,5-hexadiene and 1,7-octadiene may also be used. The diolefins will of course yield (predominantly) a di-hydroformylated product, although mono-hydroformylated may also be formed.

Hydrogen and carbon monoxide may be supplied in equimolar or non-equimolar ratios, e.g. in a ratio within the range of 8:1 to 1:4, typically 4:1 to 1:2. Preferably they are supplied in a ratio within the range of 3:1 to 1:2.

In the process of the invention, the ethylenically unsaturated starting material and the formed hydroformylation product may act as reaction diluent. Hence, the use of a separate solvent is not necessary.

Nevertheless, the hydroformylation reaction may be carried out in the additional presence of a solvent if desired. The solvent may be useful in facilitating the reaction to form the products but will not be directed to facilitating the separation of liquor produced. For example, an anisole solvent can be combined with other catalyst components so that they are readily prepared in situ in the reaction scheme described above. For advantageous use of the FFE concept, codistillation of any solvent that is present with the product alcohol is generally not desired. In order to maintain a medium for the catalyst, it is desired that any such solvent be higher boiling than the product alcohol, so that a solution of catalyst in solvent remains after distillation of the product alcohol. In some cases with very high boiling product alcohol, this is a difficult attribute to satisfy. The solvent should also be inert to the catalyst components and thermally stable under distillation conditions. Examples of suitable solvents include malonnitrile, 2-pyrrolidone, 1,5-pentanediol, dimethyl sulfoxide, and methyl terminated PEG.

The hydroformylation can be suitably carried out at moderate reaction conditions using reactors well known for their utility in hydroformylation processes. Temperatures in the range of 50 to 200° C. are recommended, preferred temperatures being in the range of 70 to 160° C. Reaction pressures in the range of 500 to 10000 kPa are preferred. Lower or higher pressures may be selected, but are not considered particularly advantageous. Moreover, higher pressures require special equipment provisions.

Reaction products, byproducts, unreacted reactants, and catalyst all leave the reactor as an effluent mixture according to this invention. They are then fed to a solventless evaporative separator. Exemplary of such evaporators are falling film evaporators (FFEs) and wiped film evaporators (WFEs). In the case of the FFE, which is the most preferred embodiment, the separator is heated by steam to between about 100 and 150° C. in the shell portion of the evaporator. In general, the falling film evaporator is a cylindrical apparatus with a heat source on the wall (the steam shell) and a cold surface in the middle of the cylinder. The product distils on the hot wall and condenses on the cold surface in the middle. The residence time of the effluent in the falling film evaporator is between about 5 seconds and 1 minute. For most product alcohols, it is satisfactory for the internal cooling surface to be a tube with cooling provided by means of circulating water.

However, refrigerated media are also acceptable, especially when the product alcohol has a relatively low boiling point. A catalyst-containing liquid stream collects in the bottom of the separator. A weir at the bottom prevents mixing between the distilled product and the residual alcohol which contains the catalyst to be recycled. One or more additional conventional separation steps (such as distillations) may also be employed in this process as will be appreciated by one of ordinary skill in the art.

The process of the invention can be used for the preparation of alcohols from internal olefins at high rate, in particular by using a catalyst system as defined above, based on palladium as the platinum group metal.

Furthermore the process is very useful for the preparation of aldehydes having a high linearity, in particular by using a catalyst system as defined above, based on platinum as platinum group metal.

The invention will be illustrated by the following examples.

EXAMPLES

A rotary evaporator was used to simulate the use of a solventless evaporative separator. Indeed, it is most exemplary of a Falling Film Evaporator. A 500 ml stirred batch autoclave was used as a reactor. The catalyst solutions comprised a ligand formed from a mixture of 1,2bis(1,4-cyclooctylenephosphino) ethane and 1,2-his(1,5cyclooctylenephosphino) ethane. These ligands are broadly representative of the class of organophosphine ligands described above. Catalyst solutions were formulated as follows:

| Catalyst | Pd Acetate (grams) | Ligand (grams) | Acid (grams) | Anisole (grams) |
|---|---|---|---|---|
| A | 0.173 | 0.310 | 0.673 MSA | 19.9 |
| B (comparative) | 0.217 | 0.367 | 0.661 TFSA | 24.9 |
| C | 0.174 | 0.311 | 0.176 MSA | 20.0 |
| D | 0.0879 | 0.159 | 0.667 MSA | 19.9 |

MSA = Methanesulfonic Acid
TFSA = Triflouromethanesulfonic Acid

In Examples 1–5, alcohols added to the feed were NEOFLEX® 90 alcohol, a brand isononanol commercially available from Shell Chemical Company, and NEODOL 23® alcohol, a brand mixture of $C_{12-C13}$ linear and branched alcohols available from Shell Chemical Company. The feed olefins used were $C_8$ isomerized butene dimer, made according to the DIMERSOL® process and NEODENE 1112® olefin, a brand $C_{11}$–$C_{12}$ olefin mixture available from Shell Chemical Company.

A 2:1 v/v mixture of NEODENE 1112® olefin and NEODOL 23® alcohol was slurried overnight at ambient temperature and atmospheric pressure with a composition of Pd acetate, MSA and ligand having the molar ratio of 1:2:1. Analysis by HPLC of a filtered sample taken from the slurry revealed that the amount of catalyst dissolved in the olefin/alcohol mixture corresponded to 0.0055 wt %, i.e. $3.67 \times 10^{-4}$ moles of palladium. Under the same conditions, when TFSA was used instead of MSA, the catalyst composition dissolves to an amount corresponding to less than 0.0005 wt %, i.e. $0.33 \times 10^{-4}$ moles of palladium. Thus, Catalyst B is not according to the present invention. All percentages are on a weight basis unless otherwise indicated.

Example 1

The autoclave was charged with 71.2 g isononanol, 1.21 g water, 3.60 g of an aqueous sodium chloride solution which contained 0.0336 g sodium chloride, and 3.41 g n-decane (as an internal standard for gas chromatographic analysis of the product alcohol). Catalyst A was added to the content of the autoclave. After being flushed the autoclave was pressurized with hydrogen and carbon monoxide in a molar ratio of 2:1 to a pressure of 690 kPa and heated to 105° C. The reaction was initiated by injecting 117.8 g $C_8$ isomerized olefin which was heated to 110° C. into the autoclave using additional hydrogen and carbon monoxide in a molar ratio of 2:1. The total pressure was 5200 kPa. Additional hydrogen and carbon monoxide in a molar ratio of 2:1 was automatically fed to the batch autoclave to replace the gas consumed in the reaction, maintaining a total pressure of 5200 kPa at all times.

Upon completion of the reaction the entire product mixture was distilled in a rotary evaporator which was heated to.130° C. The overhead product contained virtually all of the anisole, water, n-decane, and unreacted octenes. The balance (up to 60% of the original reactor charge) was isononanol. The material remaining in the unevaporated product was isononanol and catalyst solution. It was determined by gas chromatographic analysis that 93.4% of the olefin had reacted. Of the olefin which reacted, 1.50% formed octane, less than 1% formed "heavy ends" which are predominantly acetals of isononanol and isononyl aldehyde, and the balance formed isononanol.

The unevaporated product (59.8 g) was returned to the batch autoclave. Water, 4.80 g, n-decane, 3.42 g, and isononanol, 30.0 g, was added to the autoclave which was then flushed with hydrogen and carbon monoxide in a molar ratio of 2:1 to a pressure of 690 kPa and heated to 105° C. The reaction was initiated by injecting 136.3 g $C_8$ isomerized olefin. The reaction was completed as before, and the product was distilled. The overheads contained water, n-decane, and unreacted octenes. The balance (up to 60% of the original reactor charge) was isononanol. The material remaining in the unevaporated product was isononanol and catalyst solution. It was determined by gas chromatographic analysis that 93.4% of the olefin had reacted. Of the olefin which reacted, 1.52% on a molar basis formed octane, less than 1% formed "heavy ends" which are predominantly acetals of isononanol and isononyl aldehyde, and the balance formed isononanol.

The unevaporated product (98.5 g) was returned to the batch autoclave. Water, 4.80 g, n-decane, 3.42 g, and isononanol, 30.0 g, was added to the autoclave which was then flushed with hydrogen and carbon monoxide in a molar ratio of 2:1 to a pressure of 690 kPa and heated to 105° C. The reaction was initiated by injecting 102.9 g $C_8$ isomerized olefin into the autoclave using additional hydrogen and carbon monoxide in a molar ratio of 2:1. The reaction was completed as before, and the product was distilled. The overheads contain water, n-decane, and unreacted octenes. The balance (up to 60% of the original reactor charge) was isononanol. The material remaining in the unevaporated product was isononanol and catalyst (palladium, organophosphine, methanesulfonic acid, hydrogen chloride, and sodium chloride). It was determined by gas chromatographic analysis that 93.6% of the olefin had reacted. Of the olefin which reacted, 1.54% formed octane, less than 1% formed "heavy ends" which are predominantly acetals of isononanol and isononyl aldehyde, and the balance formed isononanol.

This sequence of hydroformylation and distillation reactions continued for 5 more cycles. The olefin conversions measured were 93.5, 93.2, 97.0, 92.6, and 86.8%. The paraffin formed in each cycle was 1.49, 1.66, 1.53, 1.49, and 2.42% molar. For the final iteration, heavy ends had accumulated to 2.7% by weight of the reactor product. There was no evidence of plating of palladium metal at the end of the 8 iterations, and elemental analyses confirmed that 100% of the expected palladium concentration was present in the solution.

The acid/Pd ratio (mole/mole) was 9 throughout the example.

This example illustrates that catalyst solution employing MSA as the anion source is robust, stable, and easily recoverable in a hydroformylation process employing a FFA. Further, the process results in very low make of paraffins 5 and heavy ends.

Example 2

Example 1 was repeated except that the hydroformylation reactions were conducted at 110° C. Upon completion of the first reaction it was determined by gas chromatographic analysis that 95.5% of the olefin had reacted. of the reacted olefin, 0.6% formed octane, less than 1% formed "heavy ends" which were predominantly acetals and isononanol and isononyl aldehyde, and the balance formed isononanol.

This sequence of hydroformylation and distillation reactions continued for 4 more cycles. The olefin conversions measured were 94.6, 94.21 93.2, and 92.5%. The paraffin formed in each cycle was 1.62, 1.51, 1.86, and 1.83% molar. For the final experiment, heavy ends had accumulated to 2.3% by weight of the reactor product. There was no evidence of plating of palladium metal at the end of the 5 experiments. The acid/Pd ratio (mole/mole) was 9 throughout the example.

This example further illustrates that catalyst solution employing MSA as the anion source is robust, stable, and easily recoverable in a hydroformylation process employing a FFA. Further, the process results in very low make of paraffins and heavy ends.

Example 3 (Comparative)

The autoclave was charged with 89 g isononanol, 3.50 5 g water, 4.50 g of an aqueous solution of sodium chloride which contained 0.0419 g sodium chloride, and 4.21 g n-decane (as an internal standard for gas chromatographic analysis of the product alcohol). Catalyst B was added to the content of the autoclave. After being flushed the autoclave was pressurized with hydrogen and carbon monoxide in a molar ratio of 2:1 to a pressure of 690 kPa and heated to 105° C. The reaction was initiated by injecting 149.2 g $C_8$ isomerized olefin into the autoclave using additional hydrogen and carbon monoxide in a molar ratio of 2:1. The total pressure was 5200 kPa. As in the example above, it was determined by gas chromatographic analysis that 95.4% of the olefin had reacted. Of the olefin which reacted, 1.25% formed octane, less than 1% formed "heavy ends" which are predominantly acetals of isononanol and isononyl aldehyde, and the balance formed isononanol.

This sequence of hydroformylation and distillation reactions continued for 2 more cycles. The olefin conversions measured were 96.2 and 95.8%. The paraffin formed in each cycle was 1.22 and 1.15%. Upon opening the 25 autoclave after the third hydroformylation reaction, significant plating of palladium had occurred.

The organophosphine catalyst solutions were are not robust and stable in the hydroformylation process employing a FFE when the catalysts employed TFSA as the anion source.

Example 4

The autoclave was charged with 71.2 g isononanol, 1.20 g water, 3.60 g of an aqueous solution of sodium chloride which contained 0.0336 g sodium chloride, and 2.93 g n-decane (as an internal standard for gas chromatographic analysis of the product alcohol). Catalyst C was added to the content of the autoclave. After being flushed the autoclave was pressurized with hydrogen and carbon monoxide in a molar ratio of 2:1 to a pressure of 690 kPa and heated to 105° C. The reaction was initiated by injecting 119.5 g $C_8$ isomerized olefin into the autoclave using additional hydrogen and carbon monoxide in a molar ratio of 2:1. The total pressure was 5200 kPa. As in the example above, it was determined by gas chromatographic analysis that 91.2% of the olefin had reacted. Of the olefin which reacted, 1.25% formed octane, less than 1% formed "heavy ends" which are predominantly acetals of isononanol and isononyl aldehyde, and the balance formed isononanol.

This sequence of hydroformylation and distillation reactions continued for 4 more cycles. The olefin conversions measured were 90.5, 89.31 87.4, and 83.3%. Upon opening the autoclave after the fifth hydroformylation reaction, significant plating of palladium had occurred, as confirmed by elemental analysis which revealed that 62% of the palladium had plated. The acid/Pd ratio (mole/mole) was 2.3% throughout the example.

This example illustrates that the hydroformylation process employing the organophosphine/MSA catalyst solution described above should preferably have acid/Pd ratios of 2, and more preferably greater than 2.3 for long-term stability and viability of the process.

Example 5

The autoclave was charged with 71.2 g of NEODOL 23® brand alcohol; 0.60 g water, 1.80 g of a sodium chloride solution which contained 0.0168 g sodium chloride, and 3.38 g n-tridecane (as an internal standard for gas chromatographic analysis of the product alcohol). Catalyst D was added to the content of the autoclave. After being flushed the autoclave was pressurized with hydrogen and carbon monoxide in a molar ratio of 2:1 to a pressure of 690 kPa and heated to 105° C. The reaction was initiated by injecting 119.88 g of NEODENE 1112® brand olefin which was heated to 110° C. into the autoclave using additional hydrogen and carbon monoxide in a molar ratio of 2:1. The total pressure was 5200 kPa. Additional hydrogen and carbon monoxide in a molar ratio of 2:1 was automatically fed to the batch autoclave to replace the gas consumed in the reaction, maintaining a total pressure of 5200 kPa at all times. Upon completion of the reaction, the contents were removed, and the entire product mixture was distilled in a wiped film evaporator which was heated to 155° C. The vacuum was adjusted so that approximately 60'i by weight of the contents distilled overhead. This overhead product contained virtually all of the anisole, water, n-tridecane, and unreacted olefin. The balance (up to 60% of the original reactor charge) was C12/13 alcohol with about 73% linearity. The material remaining in the unevaporated product was C12/13 alcohol and catalyst (palladium, organophosphine, methanesulfonic acid, hydrogen chloride, and sodium chloride). It was determined by gas chromatographic analysis that 99.6% of the olefin had reacted. of the olefin which reacted, 0.75% formed paraffin, less than 1% formed "heavy ends", and the balance formed C12/13 alcohol.

The unevaporated product (100.0 g) was returned to the batch autoclave. It was determined by titration that a small portion of MSA had evaporated, so an additional 0.134 g MSA was added. Water (2.40 g), n-tridecane (3.40 g), and NEODOL 235 alcohol (44.4 g) was added to the autoclave which was then flushed with hydrogen and carbon monoxide in a molar ratio of 2:1 to a pressure of 690 kPa and heated to 105° C. The reaction was initiated by injecting 90.2 g NEODENE 1112® mixed olefin which was heated to 110° C. into the autoclave using additional hydrogen and carbon monoxide in a molar ratio of 2:1. The reaction was completed as before, and the product was distilled in the wiped film evaporator. The overheads contained water, n-tridecane, and unreacted olefin. The balance (up to 60% of the original reactor charge) was C12/13 alcohol. The material remaining in the unevaporated product was C12/13 alcohol and catalyst (palladium, organophosphine, methanesulfonic acid, hydrogen chloride, and sodium chloride). It was determined by gas chromatographic analysis that 99.6% of the olefin had reacted. of the olefin which reacted, 0.78% on a molar basis formed paraffin, less than 1% formed "heavy ends", and the balance formed C12/13 alcohol.

This sequence of hydroformylation and distillation reactions continued for 2 more cycles. The olefin conversions measured were 99.4% and 99.0%. The paraffin formed in each cycle was 0.72 and 0.98%. At the end of these reactions, a very small amount of plating was evident in the autoclave.

We claim:

1. A process for the recovery of alcohols comprising hydroformylation of ethylenically unsaturated compounds with carbon monoxide and hydrogen in the presence of a catalyst system comprising:

a) a source of palladium, platinum, or nickel cations;

b) a source of anions, other than halide anions;

c) a source of at least one bidentate ligands of the formula $$R^1R^2M^1RM^2R^3R^4 \qquad (I)$$

wherein $M^1$ and $M^2$ independently represent a phosphorus, arsenic or antimony atom, R represents a bivalent bridging group containing from 1–4 atoms in the bridge, $R^1$ and $R^2$ together represent a bivalent cyclic group whereby the two•free valencies are linked to $M^1$, and $R^3$ and $R^4$ independently represent a hydrocarbyl group, or together represent a bivalent cyclic group whereby the two free valencies are linked to $M^2$;

wherein said source of cations, anions, and ligands are selected to form a catalyst system having a solubility of at least $2 \times 10^{-4}$ mole of the cation a) per liter of a liquid mixture comprising said ethylenically unsaturated compound and the hydroformylation products;

and separating the hydroformylation products from the catalyst system in a solventless evaporative separator.

2. A process according to claim 1, wherein said catalyst system further comprises a promoter d) comprising chlorides, iodides or bromides.

3. A process according to claim 2, wherein said catalyst system further comprises a co-promoter comprising water.

4. A process according to claim 3, wherein the amount of water as a co-promoter is more than 0.6 wt % based on the total weight of all ingredients in the process and up to its solubility limit under the reaction conditions.

5. A process according to claim 1, wherein the source of anions b) has a pKa value of less than 3.

6. A process according to claim 5, wherein the source of anions b) has a boiling point at atmospheric pressure which is at least 50° C. above the boiling point of the hydroformylation product.

7. A process according to claim 6, wherein the source of anions b) has a boiling point at atmospheric pressure of between 200 and 400° C.

8. A process according to claim 1, wherein the source of anions b) comprises unsubstituted alkyl sulfonic acids, aryl sulfonic acids, perfluorinated alkyl sulfonic acids, perfluorinated aryl sulfonic acids, boric acid derivatives or alkylated versions thereof.

9. A process according to claim 8, wherein the source of anions b)comprises methane sulphonic acid, perfluoro octane sulphonic acid and pentafluro benzene sulphonic acid.

10. A process according to claim 9, wherein the bidentate ligand c)comprises 1,2-bis(cyclooctylenephosphino) ethane.

11. A process according to claim 1, wherein the bidentate ligand c) carries on any of its groups R, $R^1$, $R^2$, $R^3$ and $R^4$ one or more non-polar branches.

12. A process according to claim 11, wherein the branch is chosen from the group of alkyl, cycloalkyl, aryl, alkylaryl and arylalkyl, one or more atoms of which may be a heteroatom.

13. The process according to claim 1, wherein said solventless separator comprises a falling film evaporator or a wiped film evaporator.

14. A process for the recovery of alcohols comprising hydroformylation of ethylenically unsaturated compounds with carbon monoxide and hydrogen in the presence of a catalyst system comprising:

a) a source of palladium, platinum, or nickel cations;

b) a source of anions comprising unsubstituted alkyl sulfonic acids, aryl sulfonic acids, perfluorinated alkyl sulfonic acids, perfluorinated aryl sulfonic acids, boric acid derivatives or alkylated versions thereof;

c) a source of at least one bidentate ligands of the formula

  (1)

wherein $M^1$ and $M^2$ independently represent a phosphorus, arsenic or antimony atom, R represents a bivalent bridging group containing from 1–4 atoms in the bridge, $R^1$ and $R^2$ together represent a bivalent cyclic group whereby the two free valencies are linked to $M^1$, and $R^3$ and $R^4$ independently represent a hydrocarbyl group, or together represent a bivalent cyclic group whereby the two free valencies are linked to $M^2$;

and separating the hydroformylation products from the catalyst system in a solventless evaporative separator.

15. The process according to claim 14, wherein said source of anions b) comprises methane sulfonic acid, perfluoro octane sulfonic acid or pentafluro benzene sulfonic acid.

16. The process according to claim 14, wherein said source of anions b) comprises methane sulfonic acid.

17. The process according to claim 14, wherein said solventless evaporative separator comprises a falling film evaporator or a wiping film evaporator.

18. The process according to claim 14, wherein the molar ratio of said source of anions b) to metal cations is greater than 2.3:1.

19. The process according to claim 14, wherein said catalyst system further comprises a promoter.

20. The process according to claim 19, wherein said catalyst promoter comprises a source of chloride ions.

21. The process according to claim 20, wherein said catalyst system further comprises a co-promoter comprising water in an amount of more than 0.6 wt % based on the total weight of all ingredients in the process and up to its solubility limit under the reaction conditions.

22. The process according to claim 14, wherein said source of cations a) comprises palladium; said source of anions b) comprises methane sulfonic acid, perfluoro octane sulfonic acid or pentafluro benzene sulfonic acid; said source of ligands comprises a bis(cyclooctylenephosphino) compound; the molar ratio of said source of anions b) to palladium being greater than 2.3:1, and said solventless separator comprising a falling film evaporator or a wiping film evaporator.

23. The process according to claim 22, wherein further comprising a source of chloride ions as a promoter and water as a co-promoter in an amount of more than 0.6 wt % based on the total weight of all ingredients in the process and up to its solubility limit under the reaction conditions.

* * * * *